United States Patent [19]

Wu et al.

[11] Patent Number: 5,396,022
[45] Date of Patent: Mar. 7, 1995

[54] DEFLUORINATION OF ALKANE STREAMS

[75] Inventors: An-hsiang Wu; Marvin M. Johnson; Bruce B. Randolph, all of Bartlesville, Okla.

[73] Assignee: Phillips Petroleum Company, Bartlesville, Okla.

[21] Appl. No.: 161,293

[22] Filed: Dec. 2, 1993

[51] Int. Cl.⁶ .......................... C07C 7/00; C07C 7/17; C07C 1/00
[52] U.S. Cl. .................................... 585/852; 585/856; 585/733
[58] Field of Search .......................... 585/852, 856, 733

[56] References Cited

U.S. PATENT DOCUMENTS

| | | | |
|---|---|---|---|
| 2,347,945 | 5/1944 | Frey | 260/683.4 |
| 2,403,714 | 7/1946 | Frey | 260/683.4 |
| 2,409,372 | 10/1946 | Matuszak | 196/41 |
| 2,412,726 | 12/1946 | Frey | 260/683.4 |
| 2,413,868 | 1/1947 | Frey | 260/683.4 |
| 3,253,054 | 5/1966 | Van Pool | 260/683.48 |
| 3,268,609 | 8/1966 | Nixon | 260/668 |
| 3,767,727 | 10/1973 | Chapman | 260/683.48 |
| 3,825,616 | 7/1974 | Chapman | 260/683.48 |
| 3,842,140 | 10/1974 | Hutson, Jr. et al. | 260/683.51 |
| 3,931,352 | 1/1976 | Mikulicz | 260/683.49 |
| 3,984,352 | 10/1976 | Rodewald | 252/436 |
| 4,026,961 | 5/1977 | Hutson, Jr. | 260/683.49 |
| 5,245,103 | 9/1993 | Wu | 585/743 |

OTHER PUBLICATIONS

Kozo Tanabe, "Solid Acids and Bases", 1970, Academic Press, pp. 45–50.
Herman Pines et al., "Alumina: Catalyst and Support...", Journal of the American Chemical Society 82 (1960), pp. 2471–2483.

*Primary Examiner*—Anthony McFarland
*Assistant Examiner*—Nhat D. Phan
*Attorney, Agent, or Firm*—K. K. Brandes

[57] ABSTRACT

An alkane/fluoroalkane feed is treated with an acidic alumina to reduce the amount of fluoroalkane(s) in the feed. In a particularly preferred embodiment, the feed is treated with a sulfur-containing alumina so as to convert a major portion of fluoroalkane(s) to higher alkane(s).

13 Claims, No Drawings

DEFLUORINATION OF ALKANE STREAMS

BACKGROUND OF THE INVENTION

Alkane streams (e.g., n-butane streams) from HF-catalyzed alkylation processes (e.g., the alkylation of isobutane with light olefins such as butene-2) frequently contain fluoroalkanes as impurities. Generally, sorbent materials, such as bauxite or activated alumina, are used to remove fluoroalkanes from these alkane streams. Some fluoroalkanes are not sufficiently removed by this method and may cause operational problems in downstream processes, e.g., when the above-mentioned alkane streams are used as feeds in hydroisomerization processes which employ alumina-supported, chlorided noble metal catalysts that are easily poisoned by fluoroalkanes. The present invention alleviates these problems by substantially converting undesirable fluoroalkanes to hydrocarbons which do not adversely affect downstream processes.

SUMMARY OF THE INVENTION

It is an object of this invention to remove fluoroalkanes from alkane streams which contain these fluoroalkanes as impurities. It is another objective of this invention to convert fluoroalkanes to higher alkanes. Other objects and advantages will be apparent from the detailed description of the invention and the appended claims.

In accordance with this invention, a process for removing fluoroalkanes from alkane streams comprises contacting a feed stream comprising at least one feed alkane containing 3–10 carbon atoms per molecule and at least one fluoroalkane containing 3–10 carbon atoms and 1–2 fluorine atoms per molecule with an acidic alumina (preferably gamma-alumina) at effective removal conditions.

Also in accordance with this invention, a process for removing fluoroalkanes from alkane streams comprises contacting a feed stream comprising at least one feed alkane containing 3–10 carbon atoms per molecule and at least one fluoroalkane containing 3–10 carbon atoms and 1–2 fluorine atoms with a sulfur-containing alumina which contains at least about 0.1 weight-% sulfur, at effective contacting conditions so as to convert a major portion (i.e., more than about 50%) of said at least one fluoroalkane to at least one product alkane having a higher number of carbon atoms than said at least one fluoroalkane.

DETAILED DESCRIPTION OF THE INVENTION

The term "acidic alumina", as used herein, refers to aluminas which possess surface acid sites. It is well known that certain aluminas have intrinsic surface acidity, as has been reported in the technical literature, such as in an article by Herman Pines et al. in the Journal of the American Chemical Society 82 (1960), pages 2471–2483, and in Chapter 4, pages 45–50 of Kozo Tanabe's book "Solid Acids and Bases" Academic Press, 1970 Methods for determining the surface acidity are also described in these and other publications. The surface acidity of aluminas may be due to the presence of Lewis acid sites or Bronsted acid sites or both. These acid sites are formed when aluminum hydroxide or hydrated aluminas (such as boehmite, pseudoboehmite, bayerire and the like) are calcined at a temperature in excess of about 400° C. Acidic aluminas which are employed in the process of this invention include gamma-alumina, delta-alumina, eta-alumina, theta-alumina and chi-alumina, preferably gamma-alumina.

The term "sulfur-containing alumina", as used herein, refers to acidic aluminas (such as gamma-alumina) which have been prepared in the presence of a sulfur compound, e.g., ammonium sulfate (preferred), ammonium hydrogen sulfate, ammonium aluminum sulfate, and the like, or which have been treated with an acidic sulfur-containing compound, such as sulfurous acid, ammonium hydrogen sulfite, sulfuric acid, ammonium hydrogen sulfate, ammonium sulfate, chlorosulfonic acid, fluorosulfonic acid, trifluoromethanesulfonic acid, methanesulfonic acid and the like, followed by calcining (in air or in an inert gas such as $N_2$, Ar and the like) at about 500°–700° C. for at least about 1 hour. A presently preferred method of preparing the sulfur-containing alumina is as follows: a solution of at least one water-soluble aluminum salt (such as Al sulfate, $NH_4Al$ sulfate, Al nitrate and the like; preferably aluminum nitrate) is mixed with an aqueous solution of $(NH_4)_2SO_4$, so as to provide a molar ratio of $SO_4$:Al in the combined aqueous solution (labeled "first aqueous solution") of about 0.01:1 to about 1:1. Generally, the concentration of the Al salt is about 0.1 to about 5 mol/l, and the concentration of the $(NH_4)_2SO_4$ is about 0.1 to about 5 mol/l. Then enough of an aqueous alkaline solution (i.e., a solution of NaOH or KOH or $NH_3$, preferably an aqueous solution of $NH_3$ which forms $NH_4OH$) is added to the above-described combined aqueous solution until the pH in the combined solution has been raised to a pH of at least about 8, preferably about 9–12. Generally, the concentration of alkali metal or ammonium hydroxide in the alkaline solution is about 1–20 mol/l. When enough of the alkaline solution has been added, generally with agitation, to attain a pH of at least about 8, a precipitate forms. The precipitate is believed to be an intimate mixture containing hydrated alumina (or aluminum hydroxide) and aluminum hydroxy sulfates, such as $Al(OH)SO_4$, $Al_2(OH)_4SO_4$ and $Al_2(SO_4)_3$. The precipitate is separated from the combined aqueous solution by any suitable means (preferably by filtration), washed (preferably with distilled or deionized water), dried, and then heated for at least about 1 hour (preferably about 2–8 hours) at a temperature of about 500°–700° C. (preferably at about 600°–650° C.), either in air or in an inert gas atmosphere (such as $N_2$ or He or Ar). Preferably, the sulfur content in the sulfur-containing alumina is about 0.1–3 weight-% S (as sulfate).

Preferably, the alumina materials employed in the process of this invention have a surface (determined by the BET method of Brunauer, Emmett and Teller employing $N_2$ gas) of at least about 40 m²/g, more preferably about 100–400 m²/g, a pore volume (determined by nitrogen intrusion) of about 0.3–1.0 cm³/g, and a particle size of about 8–200 mesh.

Any suitable alkane/fluoroalkane feed can be employed in the process of this invention. Generally, the feed alkanes can be normal (straight-chain) alkanes containing 3–10 carbon atoms per molecule or isoalkanes (i.e., branched alkanes) containing 4–10 carbon atoms per molecule, or a mixture of these normal and branched alkanes. Non-limiting examples of suitable alkanes are propane, n-butane, isobutane, n-pentane, isopentane (i.e., 2-methylbutane), n-hexane, isohexanes (such as 2-methylpentane, 3-methylpentane, 2,2-dimethylbutane), n-heptane, isoheptanes (in particular, methyl-substituted hexanes and dimethyl-substituted pentanes), n-octane, isooctanes (in particular, methyl-substituted heptanes and dimethyl-substituted hexanes), n-nonane, isononanes (in particular, methyl-substituted octanes and dimethyl-substitutes heptanes), n-decane and isodecanes (in particular, methyl-substituted nonanes, dimethyl-substituted octanes, trimethyl-substituted heptanes, tetramethyl-substituted hexanes). Preferred are $C_4$–$C_{10}$ alkanes, in particular those which are present in streams from alkylation processes. Particularly preferred feed alkanes are n-butane and n-pentane.

The fluoroalkanes which can be present in the alkane/fluoroalkane can be those containing one or two fluorine atoms. Generally, the feed fluoroalkane contains 3–10 (preferably 3–8) carbon atoms per molecule and 1–2 fluorine atoms (preferably 1 F atom) per molecule. Non-limiting examples of suitable fluoroalkanes include: 1-fluoropropane, 2-fluoropropane, 1-fluorobutane, 2-fluorobutane, 1-fluoro-2-methylbutane, 1,2-difluorobutane, 2,2-difluorobutane, 1-fluoropentane, 2-fluoropentane, 3-fluoropentane, 1,2,-difluoropentane, 2,3-difluoropentane, 1-fluoro-3-methylbutane, mono- and difluorohexanes, mono- and difluoroheptanes, mono- and difluorooctanes, mono- and difluorononanes, mono- and difluorodecanes, and mixtures thereof. Particularly preferred are monofluoroalkanes, more preferably 1-fluoropentane (which can be present in a n-pentane stream) and 2-fluorobutane (which can be present in a n-butane stream). Generally, the concentration of the fluoroalkane(s) in the alkane/fluoroalkane feed is relatively small: about 10–1000 ppm (parts by weight of fluoroalkane per million parts by weight of feed), preferably about 20–500 ppm fluoroalkane.

The contacting of the alkane/fluoroalkane feed with the alumina material can be carried out in any suitable manner (either in a batch process or, preferably, continuously), as a slurry operation or as a fluidized bed operation (wherein alumina particles are dispersed in the liquid feed with a suitable sorbent (e.g., bauxite, activated alumina) to remove a portion of fluoroalkanes before the contacting with the acidic and/or S-containing alumina is carried out.

The obtained liquid product has a substantially reduced concentration of fluoroalkanes (as compared with the feed). The product can be separated into various hydrocarbon fractions by well known separation means (e.g., fractional distillation), or it can be further treated with a suitable sorbent material (e.g., a molecular sieve) to remove various impurities (e.g., water, acidic compounds such as HF, olefins). Preferably, the product obtained by the process of this invention contains less than about 10 ppm fluoroalkanes and negligible amounts of olefins and hydrogen fluoride.

The following examples are presented to further illustrate this invention and are not to be construed as unduly limiting the scope of the invention.

EXAMPLE I

This example illustrates the removal of fluoroalkanes (alkyl fluorides) from alkane/fluoroalkane mixtures in the presence of various alumina materials in accordance with this invention.

Alumina A was a commercial gamma-alumina, provided by American Cyanamid Company, Wayne, N.J., under the product designation of SN-5584.

Alumina B was a commercial gamma-alumina, provided by Kaiser Aluminum and Chemical Corporation, Granary, La., under the product designation of A-305.

Alumina C was a commercial gamma-alumina, provided by Akzo Chemicals Inc., Pasadena, Tex., under the product designation of Ketjen AS-0811.

Alumina D was a commercial gamma-alumina, provided by Aluminum Company of America, Alcoa Industrial Chemicals Division, Bauxite, Ariz., under the product designation of S-100.

Pertinent properties of these four aluminas are summarized in Table I.

TABLE I

| Alumina | Surface Area $m^2/g$ | Pore Volume mL/g | Elemental Analysis | | | | | | |
|---|---|---|---|---|---|---|---|---|---|
| | | | Na Wt-% | Mg Wt-% | Al Wt-% | Si Wt-% | S Wt-% | Cl Wt-% | Mo Wt-% |
| A | 144 | 1.00 | 0.160 | 0.700 | 50.400 | 1.200 | 0.000 | 0.052 | 0.280 |
| B | 325 | 0.27 | 0.430 | 0.800 | 50.100 | 0.000 | 0.000 | 0.063 | 0.000 |
| C | 281 | 0.73 | 0.240 | 0.700 | 46.600 | 0.360 | 0.500 | 0.000 | 0.059 |
| D | 340 | 0.55 | 0.460 | 0.800 | 50.600 | 0.000 | 0.000 | 0.000 | 0.000 | feed) or as a moving bed operation or, preferably, as a fixed bed operation (wherein the liquid feed is pumped upward or downward through a fixed bed containing the alumina material). Any suitable, effective contacting conditions can be employed. Generally, the reaction temperature is about 20°–100° C. (preferably about 40°–80° C.), the pressure is about 30–600 psig, and the liquid hourly space velocity is about 1–10 cc liquid feed per cc alumina material per hour. At the preferred contacting conditions, a substantial amount of feed fluoroalkanes is substantially converted to higher alkanes, e.g., 2-fluorobutane to octanes, as is demonstrated in Example II. It is believed, even though we do not wish to be bound by this theory, that a hydrodefluorination reaction takes place and that HF which is released in this reaction is absorbed by the alumina material. It is within the scope of this invention to have hydrogen gas (e.g., at a pressure of 50–500 psig) present during the contacting of the feed with one of the above-described aluminas. It is also within the scope of this invention to pretreat the 40–200 mesh samples of Aluminas A–D were tested for their defluorination activity as follows: 0.5 gram of each alumina and 10 mL of a dry mixture of about 0.2–0.3 weight-% 1-fluoropentane and n-pentane as the remainder were placed in a sealed glass flask under a dry $N_2$ atmosphere. The mixture was kept at 40° C. for 1 hour with slight agitation. Then the flask content was analyzed by means of a gas chromatograph. Test results are summarized in Table II.

TABLE II

| Alumina | S-Content in Alumina | PPM 1-Fluoropentane in | |
|---|---|---|---|
| | | Feed | Product |
| A | 0 | 2515 | 1518 |
| B | 0 | 2515 | 822 |
| C | 0.5 | 2880 | <2 |
| D | 0 | 2515 | 250 |

Test results in Table II show that the tested gamma-aluminas were effective defluorination agents. Alumina C which contained a significant amount of sulfur (probably as sulfate) was most effective in removing a fluoroalkane from an alkane/fluoroalkane mixture.

In another test, Alumina C (containing 0.5 weight-% sulfur) was tested again for the removal of fluoroalkanes from alkane/fluoroalkane mixtures, essentially in accordance with the above-described test procedure. Test results are summarized in Table III.

rently, hydrogen gas was also passed through the alumina-filled tube. The exiting defluorinated product stream was analyzed by means of a gas chromatograph at various time intervals. Pertinent test results are summarized in Table IV and confirm the batch reactor results summarized in Table III.

TABLE IV

| Alumina Material | Volume of Alumina (cc) | Feed Alkane | Feed Fluoroalkane | ppm Fluoroalkane | Hydrogen Pressure (psig) | Reaction Temp. (°C.) | Reaction Time (Hr.) | ppm Fluoroalkane in Product |
|---|---|---|---|---|---|---|---|---|
| C1 | 10 | n-Butane | 2-Fluorobutane | 912 | 450 | 75 | 1 | 6 |
| " | " | " | " | " | " | " | 2 | 7 |
| " | " | " | " | " | " | " | 4 | 7 |
| " | " | " | " | " | " | " | 8 | 6 |
| " | " | " | " | " | " | " | 25 | 6 |
| C2 | 20 | n-Pentane | 1-Fluoropentane | 1256 | 100 | 50 | 1 | 7 |
| " | " | " | " | " | " | " | 2 | 8 |
| " | " | " | " | " | " | " | 4 | 4 |
| " | " | " | " | " | " | " | 8 | 6 |
| " | " | " | " | " | " | " | 25 | 4 |
| " | " | " | " | " | " | " | 32 | 3 |
| " | " | " | " | " | " | " | 49 | 4 |

EXAMPLE III

This example illustrates the preparation of several sulfur-containing alumina materials and their use for removing a fluoroalkane from an alkane/fluoroalkane mixture.

TABLE III

| Size of Alumina C | Alkane | Fluoroalkane | Reaction Time (Hour) | PPM Fluoroalkane in Feed | PPM Fluoroalkane in Product |
|---|---|---|---|---|---|
| 1/16 inch | n-Pentane | 1-Fluoropentane | 2 | 1681 | <2 |
| 12–18 mesh | " | " | " | " | " |
| 18–40 mesh | " | " | " | " | " |
| 40–100 mesh | " | " | " | " | " |
| 1/16 inch | n-Butane | 2-Fluorobutane | 1 | 1526 | <2 |
| 12–18 mesh | " | " | " | " | " |
| 18–40 mesh | " | " | " | " | " |
| 40–100 mesh | " | " | " | " | " |

Test results in Table III confirm those obtained for Alumina C in Table II, namely that the product contained no detectable amounts of fluoroalkanes (2 ppm was the detection limit for fluoroalkanes of the gas chromatograph).

EXAMPLE II

In this example, results of continuous flow reactor tests for defluorinating alkane/fluoroalkane feeds in accordance with this invention are described.

Alumina C was ground and sieved. A 12–18 mesh fraction (labeled Alumina C1) and a 40–100 mesh fraction (labeled Alumina C2) were collected and tested in two continuous flow tests. A U-shaped stainless steel reactor tube (inner diameter: 0.29 inch; total length: 60 inches) was filled with 10–20 cc of each of the above-described alumina materials. The reactor was heated to the desired reaction temperature. A preheated alkane/-fluoroalkane feed was pumped through the alumina-filled reactor tube at a feed rate of 60 mL/hour. Concur- To an aqueous solution containing 75.028 grams of $Al(NO_3)_3 \cdot 9H_2O$, variable amounts of $(NH_4)_2SO_4$ (see Table V), and 300 mL of deionized water was added 100 mL of an aqueous ammonium hydroxide solution containing 28 weight-% $NH_3$. A precipitate formed which was allowed to settle and age at room temperature for about 30 minutes. The aqueous slurry was filtered. The obtained solid filter cake was dried in a vacuum oven for 18 hours at 125° C. and then calcined in air for 2 hours at 600° C. Each calcined alumina material was ground and sized to 20–40 mesh.

A sample of each sized alumina material (prepared from various amounts of ammonium sulfate) was then tested for the removal of 2-fluorobutane from a feed mixture containing n-butane and small amounts of 2-fluorobutane, essentially in accordance with the procedure described in Example I. Test results are summarized in Table V.

TABLE V

| Alumina Material | Preparation of Alumina Material Wt. of $(NH_4)_2SO_4$ in Solution (g) | Preparation of Alumina Material Molar Ratio of $SO_4$:Al in Solution | PPM 2-Fluorobutane in Feed | PPM 2-Fluorobutane in Product | PPM Formed Products $C_8$ Alkanes | PPM Formed Products Olefins |
|---|---|---|---|---|---|---|
| E | 0 | 0 | 318 | 294 | Trace | 0 |
| F | 0.26 | 0.01:1 | " | 24 | 283 | " |
| G | 1.32 | 0.05:1 | " | <2 | 362 | " |
| H | 2.64 | 0.10:1 | " | " | 377 | " |
| I | 5.29 | 0.20:1 | " | " | 364 | " |
| K | 7.93 | 0.30:1 | " | " | 361 | " |

TABLE V-continued

| Alumina Material | Preparation of Alumina Material | | PPM 2-Fluorobutane | | PPM Formed Products | |
|---|---|---|---|---|---|---|
| | Wt. of (NH$_4$)$_2$SO$_4$ in Solution (g) | Molar Ratio of SO$_4$:Al in Solution | in Feed | in Product | C$_8$ Alkanes | Olefins |
| L | 13.21 | 0.50:1 | " | " | 369 | " |
| M | 18.50 | 0.70:1 | " | " | 364 | " |
| N | 26.43 | 1.00:1 | " | " | 365 | " |

Note: Only traces of alkanes other than C$_8$ alkanes were detected in the product.

Test results summarized in Table V show that only the aluminas which had been prepared in the presence of ammonium sulfate, and thus contained sulfur, were effective in removing significant amounts of 2-fluorobutane from the feed. The most effective aluminas were those that had been prepared from solutions which contained (NH$_4$)$_2$SO$_4$ and Al(NO$_3$)$_3$ at a molar SO$_4$:Al ratio of about 0.05:1 to about 1:1. Test results in Table V further indicate 2-fluorobutane had been substantially converted to an alkane containing 8 carbon atoms per molecule.

Reasonable variations, modifications and adaptations for various conditions and reactants can be made within the scope of the disclosure and the appended claims without departing from the scope of this invention.

That which is claimed is:

1. A process for removing fluoroalkanes from alkane streams which comprises contacting a feed stream comprising at least one feed alkane containing 3–10 carbon atoms per molecule and at least one fluoroalkane containing 3–10 carbon atoms and 1–2 fluorine atoms with a sulfur-containing alumina, which contains at least about 0.1 weight-% sulfur, at effective contacting conditions so as to convert a major portion of said at least one fluoroalkane to at least one product alkane having a higher number of carbon atoms than said at least one fluoroalkane.

2. A process in accordance with claim 1, wherein said sulfur-containing alumina has a surface area of at least about 40 m$^2$/g and contains about 0.1–3 weight-% sulfur.

3. A process in accordance with claim 1, wherein said sulfur-containing alumina has been prepared by a method comprising the steps of preparing a first aqueous solution containing at least one aluminum salt and ammonium sulfate at a molar SO$_4$:Al ratio of about 0.01:1 to about 1:1, adding an aqueous alkaline solution to said first aqueous solution so as to attain a pH of the combined solution of at least about 8 and to form a precipitate, separating said precipitate from the combined solution, and heating the separated precipitate at a temperature of about 500°–700° C. for at least about 1 hour.

4. A process in accordance with claim 3, wherein said aqueous alkaline solution is an ammonia solution.

5. A process in accordance with claim 1, wherein said sulfur-containing alumina has been prepared by treating an alumina with an acidic sulfur-containing compound, followed by calcining at about 500°–700° C. for at least about 1 hour.

6. A process in accordance with claim 1, wherein said sulfur-containing alumina is a gamma-alumina which has a surface area of about 100–400 m$^2$/g, and contains about 0.1–3 weight-% sulfur.

7. A process in accordance with claim 1, wherein said at least one fluoroalkane is at least one monofluoroalkane containing 3–8 carbon atoms per molecule.

8. A process in accordance with claim 1, wherein said at least one feed alkane contained in said feed stream is selected from the group consisting of n-butane and n-pentane, said at least one fluoroalkane contained in said feed stream is selected from the group consisting of 2-fluorobutane and 1- fluoropentane, and said sulfur-containing alumina contains about 0.1–3 weight-% sulfur.

9. A process in accordance with claim 8, wherein the concentration of said at least one fluoroalkane in said feed stream is about 10–1000 ppm, and said sulfur-containing alumina has a surface area of about 100–400 m$^2$/g.

10. A process in accordance with claim 1, wherein said effective contacting conditions comprise a reaction temperature of about 20°–100° C.

11. A process in accordance with claim 10, wherein said effective contacting conditions further comprise a pressure of about 30–600 psig, and a liquid hourly space velocity of about 1–10 cc feed per cc sulfur-containing alumina per hour.

12. A process in accordance with claim 10, wherein said effective contacting conditions produce a product containing less than about 10 ppm of said at least one fluoroalkane.

13. A process in accordance with claim 1, wherein the concentration of said at least one fluoroalkane in said feed stream is about 10–1000 ppm.

* * * * *